United States Patent [19]
Kita

[11] Patent Number: 6,162,801
[45] Date of Patent: Dec. 19, 2000

[54] EXTERNAL OPHTHALMIC PREPARATION CONTAINING VITAMIN D

[76] Inventor: Kiyoshi Kita, 4-4-7-502 Honmachi, Shibuya-ku, Tokyo 151, Japan

[21] Appl. No.: 09/011,622

[22] PCT Filed: Apr. 22, 1996

[86] PCT No.: PCT/JP96/01082

§ 371 Date: Feb. 12, 1998

§ 102(e) Date: Feb. 12, 1998

[87] PCT Pub. No.: WO97/18817

PCT Pub. Date: May 29, 1997

[30] Foreign Application Priority Data

| Nov. 20, 1995 | [JP] | Japan | 7-335587 |
| Dec. 13, 1995 | [JP] | Japan | 7-349929 |
| Dec. 18, 1995 | [JP] | Japan | 7-351708 |

[51] Int. Cl.[7] .................................................. A61K 31/59
[52] U.S. Cl. ............................................ 514/167; 514/912
[58] Field of Search ..................................... 514/167, 912

[56] References Cited

U.S. PATENT DOCUMENTS

| 4,335,120 | 6/1982 | Holick et al. . |
| 4,610,978 | 9/1986 | Dikstein et al. . |
| 4,923,699 | 5/1990 | Kaufman . |
| 5,254,538 | 10/1993 | Holick et al. . |
| 5,449,668 | 9/1995 | Sestelo et al. . |
| 5,622,982 | 4/1997 | Schuster et al. . |

FOREIGN PATENT DOCUMENTS

| 63-145233 | 6/1988 | Japan . |
| 1-249714 | 10/1989 | Japan . |
| 2-178218 | 7/1990 | Japan . |
| 5-503922 | 6/1993 | Japan . |
| 5-320039 | 12/1993 | Japan . |
| 5-508655 | 12/1993 | Japan . |
| WO96/29079 | 9/1996 | WIPO . |
| WO 98/18468 | 5/1998 | WIPO . |

OTHER PUBLICATIONS

International Search Report dated Jul. 9, 1996 for PCT/JP96/01082.
Sunlight . . . PRK; Sabbagh, Ocular Surgery News, vol. 9, No. 11, 1991, Slack Inc. NJ, U.S.A.
The Vitamins, pp 54–55, 104–115, 150–177, 206–221, 1992, Academic Press, Inc., CA, U.S.A.
Dryeye Brochure, pp 10–13, 1992, Nippon Hyoronsha, JPN.
Preventive Ophthalmology, pp 388–395, 1993, Appleton & Lange, CT, U.S.A.
Ganka New Insight 5, pp 132–143, 1995, Medical View-sha, JPN.
Proc. Soc. Exptl. Biol. Med., 1992;20:80–81, U.S.A.
Proc. Soc. Exptl. Biol. Med., 1992;20:81–85, U.S.A.
J. Biol. Chem., 1923;55:575–597, U.S.A.
*The Vitamins*, "Copyright page", page "v" & Contents, and pp. 24–27. Related to Reference AK of record. (1978).

*Primary Examiner*—Zohreh Fay
*Attorney, Agent, or Firm*—Staas & Halsey LLP

[57] ABSTRACT

An ophthalmic composition, containing ergocalciferol or cholecalciferol, i.e., an inactive vitamin D, as the active ingredient, for treating and conditioning damaged tissue of the region of the eye. An ophthalmic composition for preventing and treating disturbed metabolism in eye tissues, such as "dry eye", including a vitamin D or an active vitamin D as the active ingredient. An ophthalmic composition or a dermatological composition for protecting the skin or eyes from harmful ultraviolet radiation including a vitamin D or a vitamin K as the active ingredient. The ophthalmic composition normalizes the transparency or refraction of the eyeballs when administered to the region of the eye, and contributes to the amendment, healing or prevention of symptoms due to disturbed metabolism in eye tissue. The dermatological composition protects the skin and scalp from harmful ultraviolet radiation. It is possible to supply vitamin D to the skin by applying the vitamin D-containing dermatological composition via a cosmetic.

4 Claims, No Drawings

EXTERNAL OPHTHALMIC PREPARATION CONTAINING VITAMIN D

BACKGROUND OF THE INVENTION

1. Field of Invention

This invention relates to ophthalmic or dermatological compositions for external use, and more specifically, to such external medicines when used for the purpose of mediating healing of injured ocular tissue or treating ophthalmic diseases with ophthalmic compositions containing vitamin D (ergocalciferol or cholecalciferol), or for the purpose of protecting ocular tissue or skin from harmful ultraviolet rays with ophthalmic or dermatological compositions containing vitamin D or vitamin K.

2. Description of the Related Art

Vitamin D2, which is refined from vitamin D1 containing other isomers and is highly antirachitic, and vitamin D3, which was researched after vitamin D2, are often used today for the treatment of patients suffering from rickets, osteomalacia, osteoporosis, osteatis fibrosa, osteosclerosis and other bone diseases, malignant tumors such as breast and colon cancers, and skin diseases such as psoriasis. In general, the term "vitamin D" by itself is used to refer to highly antirachitic vitamin D2 (ergocalciferol) and vitamin D3 (cholecalciferol).

In general, the ultraviolet (UV) light absorption spectra of vitamin D and active vitamin D have absorption maxima near 265 nm, with molar absorption coefficients of about 18,000. Their UV light absorption bands are in the 240–290 nm range. For example, ergocalciferol, 25-monohydroxyvitamin D2, 1alpha,25-dihydroxyvitamin D2, 24,25-dihydroxyvitamin D2 and others have UV light absorption spectra with maxima near 265 nm, and molar absorption coefficients of about 18,900. In addition to these vitamins, provitamin D and previtamin D also have similar UV light absorption spectra. The provitamins D ergosterol and 7-dehydrocholesterol have respective molar absorption coefficients of 11,000 and 10,920, and UV light absorption spectra with maxima at 271, 281 and 293 nm. The previtamins D pre-ergocalciferol and pre-cholecalciferol both have molar absorption coefficients of 9,000 and UV light absorption spectra with absorption maxima at 260 nm.

Therapeutic vitamin D is administered orally or by injection, and is applied to the skin as an active vitamin D ointment in the case of skin conditions. It is known that the molecular structure of vitamin D is altered in the liver and kidneys, converting it into biologically active vitamin D. Hitherto it has been thought that the topical human use of the vitamins D ergocalciferol or cholecalciferol was useless for the treatment of local tissue, as for the treatment of psoriasis, for example.

Since the discovery of calcitriol (1alpha,25-dihydroxycholecalciferol), an active form of vitamin D which is derived from cholecalciferol, it has come to be understood that vitamin D has physiological actions other than calcium regulation. Active vitamins D formed by hydroxylation of the C1 position of the A-ring of the sterol nucleus, side-chain C25 or both C1 and C25 include calcitriol (1alpha,25-dihydroxyvitamin D), 1alpha,24-dihydroxyvitamin D, alfacalcidol (1alpha-monohydroxyvitamin D), calcifediol (25-monohydroxyvitamin D), 1alpha,24,25-trihydroxyvitamin D, 1beta,25-dihydroxyvitamin D, oxacalcitriol, calcipotriol and KH1060. Analogues include dihydrotachysterol. It is now known that there are active vitamin D receptors in the cells, and the inhibition of cell activity is being studied since active vitamin D inhibits the production of a variety of cytokines.

The known ophthalmic symptoms of vitamin deficiency include nyctalopia, Bitot's spots of the conjunctiva and xerosis of the conjunctiva and cornea resulting from vitamin A deficiency, beriberi amblyopia resulting from vitamin B1 deficiency, and diffuse superficial keratitis, retrobulbar neuritis and optic atrophy occurring in cases of vitamin B2 deficiency, as well as hemorrhaging of the eyelid, conjunctiva and retina which are seen in cases of scurvy resulting from vitamin C deficiency.

Hyperplasia occurs in the cells of the keratitis site during the process of wound recovery in postoperative corneal surgery patients, and in some cases the metabolites of hyperplastic cells may also cause corneal opacity and changes in corneal refraction. Although there are normally 5 layers of epithelial cells in the cornea, the corneal epithelium which covers the stroma may grow to about 10 layers of cells if trauma is complex and reaches into the keratocytes. When trauma reaches into the stroma, the activated keratocytes form hyperplasia and produce excess metabolites to speed healing. Although the stratified epithelial cells eventually return to normal, corneal refraction and transparency are affected by transient epithelial stratification and the metabolites of the stratified cells and activated keratocytes. Although corticosteroids are administered following corneal surgery, steroid-induced glaucoma and steroid-induced cataracts are known to occur as side-effects. Surgeries to repair an injured cornea and ophthalmic surgeries which traumatize the cornea include surgery to correct corneal refraction, cataract surgery, intraocular-lens implant surgery, pterygium surgery, surgery to remove a corneal foreign body, corneal transplantation and corneoplasty.

Corneal dystrophy occurs when metabolic abnormalities of the epithelium, keratocytes or endothelium result in the accumulation mainly of isomeric proteins in the keratocytes, causing corneal opacity. Types of corneal dystrophy include granular corneal dystrophy, macular corneal dystrophy, lattice corneal dystrophy, gelatinous drop-like dystrophy, Schnyder's corneal dystrophy and Francois's corneal dystrophy. In corneal ulceration, on the other hand, ulcers are caused by the product of excessive collagenase in the corneal epithelium. Consequently, corneal dystrophy and corneal ulceration differ in their causes and clinical signs.

It is well known that UV light is injurious to the eyes. In particular, wavelengths of 200 to 315 nm can potentially cause actinic keratitis, and in general radiation of 260 nm is known as a cause of teratogenesis and carcinogenesis in the cells. It is also well known that UV light is injurious to the skin. In particular, wavelengths of 200 to 315 nm can potentially lead to sunburn, spots and freckles. UV light at a wavelength of 260 nm is thought to be a cause of skin cancer. Moreover, existing UV blocker should not be used in or around the eyes. The stratospheric ozone layer prevents UV at wavelengths below 286 nm from reaching the surface of the earth. However, the ozone layer is said to be 2–4 mm in thickness under 1 atmosphere, it is reported that fluorine compounds and methyl bromide are destabilizing the ozone layer, and increased rates of skin cancer are being reported from South America and Australia. In general, the peak wavelength of conventional UV sterilizers is 254 nm.

On the first page of the *Ocular Surgery News*, Vol. 9, No. 11, published in U.S.A. on Jun. 1, 1991, it was reported that patients being treated after excimer laser keratectomy can experience impaired vision and edema caused by UV light.

In corneal disease patients, there is hyperplasia of the cells at the keratitis site, and corneal transparency and refraction may also be adversely affected by the metabolites of such cells. Inflammed keratocytes produce excessive metabolites. Apart from inflammation, there are also corneal diseases in which collagenase and isomeric proteins are seen as metabolites of the corneal epithelial cells and activated keratocytes. The metabolites of stratified cells affect corneal refraction and transparency. It is known that corticosteroids are not effective for treating corneal diseases in which collagenase and isomeric proteins are present. In general, corneal diseases include keratitis, corneal ulceration and corneal dystrophy.

In cataract surgery, generally extracapsular cataract extraction is performed, leaving behind the posterior capsule and the periphery of the anterior capsule. However, cells of the epithelium lentis remain inside the capsule. These residual cells gradually proliferate and spread, and they and their metabolites such as collagen may cause secondary cataracts in which there is opacity of the lenticular capsule and the patient's vision is adversely affected. A two-line drop in test types resulting from such secondary cataracts occurs among approximately 10% of cataract patients within 1 year after surgery, and among approximately 20% of patients within 2 years after surgery.

Keratoconjunctival dryness, also known as "dry eye," is a focus of dispute among ophthalmologists. In the Japanese medical journal Ganka New Insight 5, published by Medical Review, there is mention of the corneal epithelium, vitamin A deficiency and keratoconjunctivitis sicca, and vitamin D is also mentioned in connection with the epidermis. Keratoconjunctival dryness is discussed extensively in the Japanese journal Dry Eye, published by Nihon Hyoronsha. These sources state that there is a profound connection between vitamin A deficiency and diseases of the corneal and conjunctival epithelium, but they also conclude that abnormalities of the corneal and conjunctival epithelium do not occur clinically in vitamin D deficiency, and that vitamin D is not involved in the eye. The journal Dry Eye classifies "dry eye" into two separate conditions, decreased lacrimation and keratoconjunctivitis sicca, which are caused respectively by reduced lacrimation and damage to the cornea and conjunctiva. It is thought that keratoconjunctival dryness is caused partly by environmental factors including decreased nictation while watching a computer or television screen, windy days, dusty environments, ozone and nitrogen oxides. It is said that keratoconjunctival dryness occurs when some factor causes keratinization of the corneal epithelial cells, the conjunctival goblet cells and the nongoblet epithelial cells. As a result, either tears are not retained in the cornea and conjunctiva, or else an abnormal decrease in one of the three layers that form the tears (the mucin layer, lacrimal layer and oil layer) occurs as a result of inflammation of the cornea or conjunctiva, resulting in keratoconjunctival dryness. Conventional treatments for keratoconjunctival dryness include artificial tears, dry eye glasses, Chinese medicine and lacrimal punctal plugs.

Among its other effects, vitamin K acts as a blood coagulation factor. Recently the association between vitamin K and bone metabolism action is being studied. Also, it has been reported that vitamin K amplifies the bone metabolism action of vitamin D3. Vitamin K has a UV absorption band in the 240–270 nm range and is fat soluble. Vitamins K2 are the menaquinones, which have repeating side chains. More specifically, vitamin K1 has a molecular weight of 450.7 and UV absorption maxima at 242–269 and 325 nm, while vitamin K2 (menaquinone 7) has a molecular weight of 649.2 and absorption maxima at 243–270 and 325–328 nm.

SUMMARY OF THE INVENTION

The first purpose of this invention is to provide ophthalmic compositions for preventing corneal opacity and corneal refractive error following corneal trauma.

The second purpose of this invention is to provide ophthalmic compositions for treating corneal disease and preventing corneal opacity and corneal refractive error.

The third purpose of this invention is to provide ophthalmic compositions for preventing and treating keratoconjunctival dryness.

The fourth purpose of this invention is to provide ophthalmic compositions for preventing secondary cataracts after cataract surgery.

The fifth purpose of this invention is to provide ophthalmic compositions for protecting ocular tissue against harmful UV light.

The sixth purpose of this invention is to provide dermatological compositions for protecting skin against harmful UV light.

Firstly, the inventor arrived at this invention by considering that when a form of vitamin D which is not yet active, that is, ergocalciferol or cholecalciferol, is applied topically to the eye, it enters cells that need to be regulated, is converted to an active form, and either induces the differentiation of those cells, or else regulates the various proteins which are produced by the cell in the cytoplasm. Consequently, in this invention the vitamin D ergocalciferol or cholecalciferol as an effective ingredient is administered directly to the eye to regulate wound healing of ocular tissue and prevent or treat corneal dystrophy or keratoconjunctival dryness. This invention provides an ophthalmic composition which regulates healing of traumatized ocular tissue after ophthalmological surgery including surgery to repair an injured cornea, surgery to correct corneal refraction, cataract surgery, intraocular-lens implant surgery, pterygium surgery, surgery to remove a corneal foreign body, corneal transplantation and corneoplasty, and which also cures granular corneal dystrophy, macular corneal dystrophy, lattice corneal dystrophy, gelatinous drop-like corneal dystrophy, Schnyder's corneal dystrophy and Francois's corneal dystrophy and other forms of corneal dystrophy, and prevents corneal opacity and corneal refractive error.

Secondly, the inventor arrived at this invention by considering that all K vitamins or vitamins D including provitamins D and vitamin D metabolites would be safe for human use if used externally to absorb the UV light which is thought to be harmful to the human body.

Keratoconjunctival dryness, also called "dry eye," is caused partly by environmental factors including decreased nictation, windy days, dusty environments, ozone and nitrogen oxides. As a result, there is keratinization of the corneal epithelial cells, the conjunctival goblet cells and the nongoblet epithelial cells. Such keratoconjunctivitis sicca reduces tears, resulting in keratoconjunctival dryness. Therefore, these are the ophthalmic compositions for preventing or treating keratoconjunctival dryness, having either vitamin D, active vitamin D or one of their analogs as its effective ingredient. Effective forms of vitamin D include ergocalciferol or cholecalciferol as well as active forms of vitamin D formed by hydroxylation of the C1 position of the A-ring of the sterol nucleus, side-chain C25 or both C1 and C25. The active vitamin D analog dihydrotachysterol also falls in the category of ophthalmic compositions for preventing or treating keratoconjunctival dryness.

In the vitamin D medicine of this invention, vitamin D is applied not for its antirachitic activity, but in order to induce differentiation of conjunctival goblet cells, conjunctival nongoblet epithelial cells and corneal epithelial cells which have keratinized or are about to keratinize in cases of keratoconjunctival dryness. In other words, the administered vitamin D has no effect on intact cells, but it induces the differentiation of conjunctival goblet cells, conjunctival nongoblet epithelial cells and corneal epithelial cells which are affected by keratoconjunctivitis sicca. The induction of differentiation of these cells by active vitamin D is thought to occur when active vitamin D attaches directly to vitamin D receptors within the cells, forming a complex which enters the nucleus and affects the DNA, so that the cells' activities are regulated.

DESCRIPTION OF THE PREFERRED EMBODIMENTS

The regulation of cell activity and the induction of cell differentiation by topical ophthalmic administration of the vitamin D ergocalciferol or cholecalciferol having been confirmed in animal experiments, this invention is aimed at maintaining eye transparency and normal refraction and preventing decreased visual function by direct topical ophthalmic administration to patients suffering from ocular trauma and eye disease. The ocular cells which are regulated by vitamin D, especially in the anterior segment of the eye, include corneal epithelial cells, keratocytes and fibroblasts, endothelial cells, conjunctival goblet cells, conjunctival nongoblet epithelial cells, epithelium lentis cells and intraocular phagocytes. Topical administration of even inactive vitamins D ergocalciferol or cholecalciferol is recognized as being effective in healing inflammation and metabolic abnormalities of these cells. In order to prevent optical transparency impairment and refraction error caused by cell hyperplasia and cell metabolites while the eye is recovering from ocular tissue damage extending below the corneal epithelium and corneal metabolic abnormalities, the vitamin D ergocalciferol or cholecalciferol is used as the effective ingredient in an ophthalmic composition. Normally, orally ingested vitamin D is converted to active vitamin D in the liver or kidneys, but the vitamin D composition of this invention acts locally in the eye. The cells which are activated, keratinized or metabolically abnormal use their own vitamin D hydroxylase to convert the vitamin D which enters the cell into active vitamin D, which either affects DNA in the nucleus and induces cell differentiation, or else affects cellular RNA and influences protein synthesis, thus regulating cell hyperplasia, excess metabolite production and keratinization in these cells. For example, in this invention the fact that epithelium and fibroblasts which were differentiated from keratocytes have enzymes which convert the administered vitamin D to active vitamin D is considered and used as a means of resolving the issues described above as the first, second and third purposes of the invention. Namely, carbon C1 or C25 of the administered vitamin D is hydroxylated by the mitochondria or microsome enzymes of the fibroblasts, producing the active vitamin D which is necessary for the regulation of those cells. The amount of vitamin D which is activated depends on the activated keratocytes and the number of their differentiated fibroblasts. In other words, the keratocytes convert vitamin D to active vitamin D, but it was discovered that when the corneal stroma is traumatized, the activated keratocytes begin to differentiate and produce fibroblasts, and the rate of conversion of vitamin D into active vitamin D increases. In patients who have undergone corneal surgery, there is an obvious increase in fibroblasts in the corneal stroma. In order to prevent postsurgical changes in corneal refraction and corneal opacity, which are caused by such an increase, an eyedrop medication for example is administered to the eye after surgery to regulate the activity of the corneal epithelial and stromal cells, with the aim of inhibiting hyperplasia and excess metabolite production in the activated corneal epithelial and stromal cells and preventing a decrease in visual acuity because of corneal opacity and changes in corneal refraction. In the area of surgeries to correct corneal refraction, the ophthalmic compositions of this invention would probably not be appropriate in cases of refractive correction aimed at changing refraction by scar hyperplasia of the keratotomy incision site. In the area of cataract surgery, the administration of the ophthalmic compositions of this invention to postsurgical patients would mitigate the opacity caused by epithelial lens cells of the lenticular capsule. This invention provides an ophthalmic composition, containing the vitamin D ergocalciferol or cholecalciferol or one of their analogs as its effective ingredient, for preventing opacity of the lenticular capsule after cataract surgery.

Moreover, vitamin D is used in this ophthalmic composition to protect ocular tissue against UV light, taking advantage of the fact that vitamin D has a maximum UV light absorption spectrum in the neighborhood of 260 nm. Effective forms of vitamin D include ergocalciferol and cholecalciferol or their analogs, and active forms of vitamin D formed by hydroxylation of the C1 position of the A-ring of the sterol nucleus, side-chain C25 or both C1 and C25 or their analogs. The active vitamin D analog dihydrotachysterol also falls in this category. The fifth purpose of this invention is achieved in this way.

As an ophthalmic composition having fat-soluble vitamin D as its effective ingredient, one characteristic of this invention is that it improves optical refraction and transparency of the patient's cornea when administered topically to the eye. The ophthalmic composition can also be formed by diluting vitamin D in an ophthalmic physiological buffer solution in which the solvent medium is ethanol, ether or a surfactant such as lecithin or polysorbate. Since vitamin D is fat-soluble, the ophthalmic composition may contain vitamin D dissolved in a plant oil such as sesame oil or fat.

The concentration of vitamin D in the prophylactic or therapeutic ophthalmic composition of this invention, since it is intended for topical administration, may be about 100 micrograms/ml or less, or at least about 0.001 micrograms/ml. The volume of one eyedrop is normally about 20–40 microliters. The concentration of active vitamin D in the ophthalmic composition should be 1 microgram/ml or less. In other words, the inventor considered that the topical administration of more than the optimum dose of active vitamin D would naturally result in a greater than optimum dose of active vitamin D for the cells. The cells themselves would then produce more hydroxylase to metabolize the active vitamin D, and the result might be a reduction in the intended therapeutic effect. When the ophthalmic composition of this invention is administered to the eyes of ophthalmological patients, the enzymes inside the activated keratocytes convert the vitamin D ergocalciferol or cholecalciferol into the necessary dose of active vitamin D. This active vitamin D then attaches to the receptors of the activated keratocytes and epithelial cells themselves or neighboring cells and influences the DNA and RNA of those cells, inducing the differentiation of the cells and regulating various cytokines, proteins and other exudates.

Since the vitamins D ergocalciferol and cholecalciferol are not cytotoxic, it is thought that they will not affect normal cells unless administered at abnormal concentrations. Even when the ophthalmic composition of this invention is administered to the eyes of ophthalmological patients, the vitamins D ergocalciferol and cholecalciferol are unlikely to reach the posterior segment of the eye. If treatment of the posterior segment of the eye with vitamin D is considered in the future, it will probably be effective to use it in combination with oral administration. Vitamin D easily permeates the cornea, which is known to be permeable to pharmaceuticals which is hydrophobic and have a smaller molecular size. For example, the molecular size of cholecalciferol is 384.6 daltons.

Vitamin D in tears on the cornea and conjunctiva or vitamin D which has penetrated into the cornea or conjunctiva significantly absorbs harmful UV radiation. The vitamins D ergocalciferol and cholecalciferol and their analogs are effective in preventing actinic keratitis and pterygium. Moreover, since UV light may be especially harmful to the eyes after excision of the human corneal Bowman's layer, as happens in refractive excimer laser keratectomy, for example, the ophthalmic composition of this invention containing vitamin D which absorbs harmful UV light will be effective.

*Ocular Surgery News* reported that patients being treated after excimer laser keratectomy can experience impaired vision and edema caused by UV light.

The vitamin D in the ophthalmic composition of this invention can be attached to or encapsulated in an ophthalmological drug delivery system. Such systems include liposomes, microspheres, protein gels, collagen or therapeutic soft contact lenses. The vitamin D in this invention can be mixed with at least one of the viscous materials polyvinyl alcohol, methylcellulose, hyaluronate, chondroitin sulfate, collagen, fatty acid, plant oil or fat, and used as a viscous ophthalmic solution. Appropriate formulations include eyedrops, ointment and contact lenses in particular.

In patients who have undergone keratectomy or keratotomy, the corneal epithelial cells spread on the corneal stroma after surgery, and the deficient epithelial cells on the stroma are regenerated within a few days. Although epithelial cell regeneration occurs, however, hyperplasia and increased cell activity also occur in the epithelial and keratocytes on the periphery of a corneal excision or at the site of a complex excision. Scar formation caused by the metabolites of such corneal epithelial and activated keratocytes exerts traction, resulting in corneal refractive error and opacity leading to reduced visual acuity. Corticosteroids are mainly used to prevent this, but there is a tendency to avoid the use of steroids because of fears that they will cause steroid-induced glaucoma and steroid-induced cataracts as side effects. By regulating hyperplasia and cell activity in the activated corneal epithelial and keratocytes by administration of the vitamin D of this invention to patients after keratotomy or keratectomy, decreased vision due to corneal refractive error and opacity is prevented. Ocular administration of the vitamin D of this invention does not have any obvious accelerating effect at least on the speed of corneal epithelial cell regeneration.

The ophthalmic composition containing vitamin D of this invention is administered to patients in order to prevent loss of transparency in human ocular tissue as a result of hyperplasia and excess metabolite production in traumatized tissue, and maintains the transparency of the eye by regulating cell activity in the traumatized tissue. Drugs such as antibiotics, antimicrobials, antiphlogistics and glaucoma drugs are used in combination after ophthalmic surgery and for treating eye disease, and it is thought that no toxicity occurs as a result of combined use with the vitamins D ergocalciferol and cholecalciferol.

Japanese Patent Publication No. 4-43887 applies the calcium metabolism action of active vitamin D, and states that active vitamin D is effective in preventing and treating cataracts. The present invention uses not active vitamin D but the vitamin D ergocalciferol or cholecalciferol for the purpose of reducing opacity of the lenticular capsule due to hyperplasia and metabolites of the lens epithelium after cataract surgery.

The vitamin D, active vitamin D, vitamin K etc. of this invention may be either natural or artificially synthesized compositions or their analogs. Analogs of the vitamin D cholecalciferol include cholecalciferol sulfate (molecular weight 486.7 daltons), while artificially synthesized active vitamin D analogs include alphacalcidol (1alpha-monohydroxyvitamin D), 22-oxacalcitriol (OCT), calcipotriol (MC903), KH1060 and dihydrotachysterol. Tears are amphipathic and viscous. If the vitamin D ophthalmic solution of this invention is mixed in a solution of polysorbate, polyvinyl alcohol, methylcellulose, hyaluronate, chondroitin sulfate, vegetable oil or fat to form viscous eyedrops, the vitamin D will remain on the surface of the eye for a long time, and will be highly effective in preventing and treating eye injuries, dry eye syndrome and ocular diseases.

Taking advantage of the fact that D vitamins have a maximum UV absorption curve for harmful UV radiation in the neighborhood of 260 nm, one or more of provitamin D, previtamin D, vitamin D, active vitamin D, vitamin K or an analog of any of these is used as the effective ingredient in the ophthalmic composition or dermatological composition. Effective forms of vitamin D include ergocalciferol or cholecalciferol as well as active forms of vitamin D formed by hydroxylation of the C1 position of the A-ring of the sterol nucleus, side-chain C25 or both C1 and C25. Considering that active vitamin D medicines have been used to treat psoriasis in the past, it is anticipated that the dermatological composition of this invention will be good for the skin. Vitamin K also has a maximum UV absorption spectrum for UV radiation in the neighborhood of 260 nm, and this fact can be exploited in making a dermatological or ophthalmic composition for protecting the eyes and skin from harmful UV radiation. The tissues in the eye which are protected from harmful UV radiation by the use of the ophthalmic composition of this invention are the cornea, conjunctiva, lens or retina. The ophthalmic composition which protects against this harmful UV radiation should preferably be in the form of an eyedrop medication, ointment or contact lenses. The dermatological composition of this invention can also be used on the hair and scalp, and it can be applied as a hair and scalp treatment conditioner or as a hair treatment conditioner.

This invention comprises at least one of the fat-soluble vitamins provitamin D, previtamin D, vitamin D, active vitamin D, vitamin K or an analog of one of these mixed in a cosmetic or sunscreen, and applied topically to the skin in order to prevent exposure of the skin to harmful UV in the neighborhood of 260 nm. This invention is a dermatological composition which takes the form of the solution, ointments, creams, lotions, sprays and treatment conditioners which have conventionally been used in cosmetics and sunscreens. Since the use of cosmetics on the skin inhibits the skin's synthesis of vitamin D by UV light, it is also possible to supplement vitamin D through the skin using the dermatological composition containing vitamin D adapted to a cosmetic.

When used on the scalp, it also protects the cuticula pili from UV light, regulates the cuticula pili activity, and prevents hair loss. In other words, the use of conventional dermatological compositions interferes with the synthesis of vitamin D in the skin. One way of supplying vitamin D to the skin is through the topical use of the dermatological composition containing the vitamins D ergocalciferol and cholecalciferol of this invention on the skin and hair. The concentration of provitamin D, previtamin D, vitamin D, active vitamin D or vitamin K in the ophthalmic or dermatological composition for protecting against harmful UV radiation of this invention, since it is intended for topical administration, may be about 100 micrograms/ml(g) or less, or at least about 0.01 micrograms/ml(g). Since provitamin D, previtamin D, vitamin D, active vitamin D and vitamin K are not cytotoxic, they should not affect the ocular tissue or epidermal cells if used in a normal mixture. When the ophthalmic composition or dermatological composition of this invention is used, the provitamin D, previtamin D, vitamin D, active vitamin D or vitamin K which covers the eyes or skin absorbs a significant amount of harmful UV radiation, and protects ocular and skin tissue from harmful UV radiation. If conventional vitamin D and active vitamin D preparations are taken orally in large doses, symptoms of vitamin D excess occur. Calcium and phosphates rise in the blood, and there is calcification of the kidneys, arteries, smooth muscles, lungs and other soft tissues. The provitamin D, previtamin D, vitamin D, active vitamin D and vitamin K of the ophthalmic or dermatological compositions of this invention have always been effective in smaller doses, and though some of the vitamin D or vitamin K may be absorbed into the blood through the eyes or skin, the side-effects seen with conventional preparations are unthinkable.

The provitamin D, previtamin D, vitamin D, active vitamin D or vitamin K of this invention may be either a natural or artificially synthesized composition, or it may be an analog. Vitamin K analogs which have been developed include the artificially synthesized, water-soluble menadiol diphosphate and menadione hydrogen sulphite salt, and these vitamin K analogs may also be used.

In U.S. Pat. No. 4,335,120, Holick et al disclose a way of introducing active vitamin D into the bloodstream through the skin for therapeutic purposes. By contrast, the present invention is a cosmetic or other dermatological composition which uses vitamin D to protect the skin against UV radiation.

In U.S. Pat. No. 4,610,978, Dikstein et al disclose active vitamin D as a skin cream for treating the skin. By contrast, the present invention is a cosmetic or other dermatological composition which uses vitamin D to protect the skin against UV radiation.

In U.S. Pat. No. 5,254,538, Holick et al disclose a method of treating periodontal disease and ulcerative keratitis and corneal abrasion in ophthalmology with active vitamin D.

The present invention contains an ophthalmic or dermatological composition which uses vitamin D to protect the eyes and skin against UV radiation. Based on the discovery that the vitamins D ergocalciferol and cholecalciferol, rather than active vitamin D, are effective in regulating wound healing as it relates to optical transparency and refraction locally in the eye, the inventor arrived at the invention of an ophthalmic composition of the vitamin D ergocalciferol or cholecalciferol. The present invention involves an ophthalmic composition of the vitamin D ergocalciferol or cholecalciferol for purposes such as preventing and treating keratoconjunctival dryness and corneal disease or preventing opacity of the posterior capsule.

Without further elaboration, it is believed that one skilled in the art, using the preceding description, can utilize the present invention to its fullest extent. The following preferred specific embodiments are, therefore, to be construed as merely illustrative, and not limitative in any way whatsoever, of the remainder of the disclosure.

This invention is explained in more detail below using examples of preparations and experiments.

PREPARATION 1

One milligram of vitamin D (cholecalciferol, molecular weight 384.6 daltons) was diluted with 10 ml of ethanol (purity 99.9%), and 0.1 ml of the diluted solution was again diluted 100-fold with a polysorbate80 ophthalmic solution (0.5%-Tween80 ophthalmic physiological buffer solution) as the vehicle, to prepare an ophthalmic composition with a vitamin D concentration of 1 microgram/ml.

PREPARATION 2

Five milligrams of vitamin D (cholecalciferol) was diluted with 10 ml of ethanol (purity 99.9%), and 0.1 ml of the diluted solution was again diluted 100-fold with an ophthalmic oil base consisting of refined sesame oil, to prepare an ophthalmic composition with a vitamin D concentration of 5 micrograms/ml.

PREPARATION 3

Five milligrams of vitamin K2 (menaquinone 4, molecular weight 444.7 daltons) was diluted with 10 ml of ethanol (purity 99.9%), and this diluted solution was again diluted 100-fold with an ophthalmic oil base consisting of refined sesame oil, to prepare an ophthalmic composition with a vitamin K concentration of 5 micrograms/ml for blocking UV radiation.

PREPARATION 4

0.5 milligrams of active vitamin D (calcitriol, 1alpha,25-dihydroxyvitamin D) was diluted with 10 ml of ethanol (purity 99.9%), and 0.1 ml of this diluted solution was again diluted 100-fold with polysorbate80 ophthalmic solution (0.5%-Tween80 ophthalmic physiological buffer solution), to prepare an ophthalmic composition with an active vitamin D concentration of 0.5 micrograms/ml which would be a prophylactic and treatment for keratoconjunctival dryness.

PREPARATION 5

One hundred milligrams of vitamin D (cholecalciferol) was diluted with 10 ml of ethanol (purity 99.9%), and 1 ml of the diluted solution was again diluted 100-fold with simple hydrophilic petrolatum (3%-cholesterol, 3%-stearyl alcohol, 8%-white wax, 86%-white petrolatum), to prepare a dermatological composition with a vitamin D concentration of 100 micrograms/ml which protects the skin against UV radiation.

PREPARATION 6

Ten milligrams of vitamin D (cholecalciferol) was diluted with 10 ml of ethanol (purity 99.9%), and 0.1 ml of the diluted solution was again diluted 100-fold with polysorbate80 ophthalmic solution (0.5%-Tween80 ophthalmic physiological buffer solution) as the vehicle, to prepare an ophthalmic composition with a vitamin D concentration of 10 micrograms/ml.

PREPARATION 7

Ten milligrams of vitamin D (cholecalciferol) was diluted with 10 ml of ethanol (purity 99.9%), and 0.1 ml of the diluted solution was again diluted 100-fold with medium-chain fatty acid triglyceride, to prepare an ophthalmic composition with a vitamin D concentration of 10 micrograms/ml.

EXPERIMENT 1

The effectiveness and safety of the vitamin D cholecalciferol in the wound healing process following corneal trauma were investigated.

Four albino rabbits weighing 2 kg each were used. After instillation anesthesia and injection of an analgesic and anesthetic to the tensor muscle, a trephine 5 mm in diameter was used to make a circular scar in about half a layer of the surface of the right cornea of each rabbit. The corneal epithelium and superficial stroma within the circle were then abraded with a spatula, and the epithelial cells removed. The left eyes were not treated. After surgery, an ophthalmic solution and ointment containing the antibiotic ofloxacin were administered to the right eyes. Two rabbits were put in group A, and the remaining two were put in group B. An ophthalmic composition prepared as in Preparation 1 was administered to group A three times a day at 4-hour intervals beginning on the following day of surgery. About 20 microliters (1–2 drops) was administered each time. An ophthalmic physiological buffer solution without vitamin D was administered to group B in the same way, three times a day at 4-hour intervals. The degree of corneal opacity in all treated eyes was observed after 1 week, 2 weeks and 1 month, using a slitlamp microscope, and evaluated at 6 levels on a scale of 0 (no corneal opacity) to 5 (serious corneal opacity).

After one week, the evaluation was 0 for groups A and B. After 2 weeks, a very slight opacity was seen subepithelially in two eyes in group B. In particular, a very slight cloudiness was seen here and there in the area traumatized by the trephine, and this was graded as 1. A very slight subepithelial opacity was seen in one eye in the A group and graded as 1, but there was no opacity in the other eye and it was graded as 0. After one month there was moderate subepithelial opacity in one eye in the B group, which was graded as 3. There was slight cloudiness in the other eye in the B group, which was graded as one. There was slight subepithelial opacity in 1 eye in the A group which was graded as 1, but there was no opacity in the other eye, which was graded as 0. After one month, opacity was visible to the naked eye in the one eye in the B group which was graded as 3, and the area inside the circle was slightly cloudy.

EXPERIMENT 2

The effectiveness and safety of the vitamin D cholecalciferol in the wound healing following corneal trauma were investigated.

Four Japanese albino rabbits weighing 2 kg each were used. Under anesthesia, an excimer laser (Summit Technology, Inc., U.S.A.) was used to irradiate the central portion of the right corneas. Irradiation was done in phototherapeutic keratectomy (PTK) mode, at energy density 165 mj/cm2, ablation rate 0.25 microns/pulse, 300 shots, ablation zone diameter 4.5 mm. The four irradiated rabbits were divided into 2 groups of 2 rabbits each, which were designated the treatment group and the control group. Antibiotics were administered to the eyes of all rabbits on the day of surgery and the following day. A vitamin D solution (cholecalciferol 10 micrograms/ml) as described under Preparation 7 was administered to the surgically treated eyes of each rabbit in the treatment group, while a base (medium-chain fatty acid triglyceride) without vitamin D was administered to the control group. Twenty microliters each time were administered three times a day for 14 days, beginning 24 hours after laser irradiation. The degree of corneal opacity was evaluated based on corneal findings in the four eyes, which were observed by slitlamp microscopy after dilation with a mydriatic 7 and 15 days after laser irradiation of the corneas. Evaluation was done by scoring the periphery and central area of the irradiated region at five levels on a scale of 0 (no corneal opacity) to 4 (complete opacity).

After 7 and 15 days, opacity was observed throughout the irradiated regions of the corneas of the control group. The degree of opacity was high at the periphery of irradiation and low in the central area. Although a circular opacity about 1 mm in width was observed at the periphery of irradiation in the treatment group, the central area was mostly clear. The average scores for the entire irradiated region were 3 in the control group and 1 in the treatment group after 7 days, and 3 in the control group and 1 in the treatment group after 15 days. Therefore, the scores of the treatment group were significantly lower than those of the control group.

For purposes of regulating corneal wound healing, the effects of the viscous ophthalmic composition of this invention were better than those obtained using a less viscous, watery base in similar tests. The effects of the vitamin D cholecalciferol in regulating corneal wound healing have also been confirmed by this Experiment 2. In Experiment 2, the rabbits were sacrificed and their eyeballs extracted. A comparative histological study of the corneas revealed that there was less hyperplasia of the epithelial cells on the periphery of irradiation in the treatment group than in the control group. These findings matched those of the slitlamp microscope examination. This shows that administration of the ophthalmic composition of vitamin D of this invention offers the advantages of reducing corneal opacity and corneal refractive error, and making it possible to avoid repeated surgery due to inadequate refractive correction after surgery in laser keratectomy patients.

EXPERIMENT 3

The effects of active vitamin D on eyes afflicted with dry eye syndrome was investigated.

Six Sprague-Dawley strain rats were used three weeks after birth. All rats were fed vitamin A-deficient diet for four weeks in order to induce a dry eye condition. Beginning in the 5th week, three rats were put in group D and given vitamin A-deficient diet, and the active vitamin D of Preparation 4 for prevention and treatment of keratoconjunctival dryness was administered. The remaining three rats were put in group C (the control group) and given vitamin A-deficient diet, and an ophthalmic composition consisting of 0.5%-polysorbate80 (Tween80) ophthalmic physiological buffer solution without active vitamin D was administered. Administration was done in both eyes three times a day by taking about 20 microliters in a pipette and administering it as 1–2 drops each time.

Two weeks after the beginning of instillation, slitlamp microscopy observation with fluorescein sodium staining revealed no superficial punctate keratitis in group D, while in the eyes in group C there were faint stained spots within a circle about 2 mm in diameter in the central portion of the cornea. In this slitlamp microscopy examination, it was found that the inflammation of superficial keratitis was greater in the C group than in the D group. The C group rats were less lively and had less excrement than the D group rats. The experiment was concluded in the fifth week. The results showed that protection and treatment of keratoconjunctival dryness was slightly better in the D group than in the C group, and the cornea and conjunctiva were better protected.

EXPERIMENT 4

The effects of UV light on the corneas, eyelids and ocular mucous membranes were investigated.

Six Sprague-Dawley strain rats were used. The two rats in the D group were given vitamin D, the two in the Group K were given vitamin K2, and the two in Group C were the control. The vitamin D ophthalmic composition of Preparation 2 was administered to Group D. Group C (the control) received ophthalmic refined sesame oil. Administration was done in both eyes three times a day by taking about 10 microliters in a pipette and administering it as 1 drop each time, beginning one week before UV irradiation. UV irradiation was done using a convention UV light sterilizer (15W discharge tube, peak UV wavelength 254 nm), and the rats were kept in this sterilizer.

On the second day in the sterilizer, slitlamp microscopy examination revealed mild superficial punctate keratitis in all eyes in Group C. Extremely mild superficial punctate keratitis was seen in all eyes in Groups D and K. On the third day in the sterilizer, there was serious eyelid and conjunctival edema and superficial punctate keratitis in all eyes in Group C, while mild conjunctival edema and superficial punctate keratitis were seen in all eyes in Groups D and K. The experiment was terminated open observation of serious eyelid and conjunctival edema and superficial punctate keratitis in the C group, and slitlamp microscopic observation with fluorescein staining was not performed. The results showed that there was clearly much better protection against UV radiation in the D and K groups than in the C group, with ocular tissues such as the eyelids, conjunctiva and cornea being protected.

EXPERIMENT 5

The degree of lenticular capsule opacity after cataract surgery was investigated using rabbits.

Four Japanese albino rabbits weighing 2 kg each were used. The right eyes of the rabbits were dilated with a mydriatic in preparation for surgery. After instillation anesthesia and injection of an analgesic and anesthetic to the tensor muscle, the corneas of the rabbits' right eyes were punctured, the anterior chamber was filled with a viscoelastic material, and anterior capsulotomy was performed to ablate a capsule about 5 mm in diameter and as round as possible. Next, an incision 3.5 mm in width was made at an angle of about 45 degrees to the corneal tangent to create a flap in the cornea about 2 mm from the corneoscleral border. Phacoemulsification was performed, the lens nucleus and cortex were removed by aspiration, the anterior chamber and the inside of the capsule were irrigated with perfusate, and surgery was terminated without suturing of the corneal incision. In an effort to prevent fibrin precipitation and a transitory rise in intraocular pressure immediately after surgery, antithrombin III was mixed to be 50 IU/ml with the viscoelastic material and perfusate used during surgery. Antibacterial ointment and eyedrops were administered to the conjunctivas and corneas of the surgically treated eyes after surgery. The ophthalmic composition of Preparation 6 was administered to the eyes of 2 rabbits which were assigned at random to the treatment group, while the other 2 rabbits were assigned to the control group and received ophthalmic composition consisting of 0.5%-polysorbate80 (Tween80) ophthalmic physiological buffer solution without vitamin D. Administration was done by taking about 20 microliters in a pipette and administering it in one dose three times a day to the surgically treated eyes.

The preceding examples can be repeated with similar success by substituting the generically or specifically described reactants and/or operating conditions of this invention for those used in the preceding examples. Antibiotics were administered three times a day and mydriatics once a day to the surgically treated eyes, each for a period of three days after surgery.

Slitlamp microscopy of surgically treated eyes dilated with mydriatics two weeks after surgery revealed bands of cloudiness in all eyes on the periphery of the torn anterior capsule. The degree of cloudiness in the treatment group was about half that in the control group, and the bands were significantly narrower in the treatment group. The lenticular capsule in the pupillary zone was also more transparent in the treatment group. Strong cloudiness of the unattached areas of the anterior and posterior capsule was observed especially in the control group. In one of the rabbits in the control group, the incised posterior surface of the cornea adhered to the anterior surface of the iris, and the pupil was deformed. The corneal wounds were more transparent in all animals in the treatment group than in the control group, and there was less scarring. When the rabbits were anesthetized and scarring was investigated by measuring astigmatism within an area 3 mm in diameter from the center of the cornea using a keratoscope, astigmatism was an average of 1.5 diopters in the treatment group and 2.5 diopters in the control group. These corneal and capsular findings indicate that the vitamin D cholecalciferol prevents cloudiness of the cornea and lenticular capsule and refraction error of the cornea when used topically in the eye.

In Experiments 1–5, the inventor observed no side-effects such as corneal opacity caused by calcium adsorption on the cornea, conjunctival congestion, fibrin precipitation in the interior chamber or endophthalmitis which might have been caused by vitamin D or vitamin K. It has been confirmed that topical ophthalmic administration of vitamin D according to this invention regulates the activity and metabolism of activated corneal epithelium, keratocytes and epithelium lentis cells during the process of wound healing, and suppresses excess metabolite production by such cells. Moreover, it was suggested that by application of the ophthalmic composition of this invention, vitamin D on the eyelids, conjunctiva and cornea and in corneal tissue significantly protects these tissues against harmful UV radiation. In addition, the fact that it protects eyelids and conjunctiva against UV confirms that it can be a dermatological composition.

The test results described above suggest that the ophthalmic or dermatological compositions of this invention would also be both safe and effective for humans. Protection and treatment of keratoconjunctival dryness of the eye can be achieved by topical ophthalmic use of either the vitamin D or active vitamin D of this invention. Moreover, better results are achieved with the ophthalmic composition if it is mixed with a solution similar to tears, such as a viscous solution.

Topical ophthalmic administration of the vitamin D composition of this invention can be applied to wound healing after ocular surgery. It is possible to prevent opacity and refractive error of the cornea and protect against harmful UV radiation by application of the vitamin D composition of this invention after keratotomy or keratectomy, thus preventing decreased visual acuity. It is also possible to avoid the side effects that have been a problem in the past with corticosteroid eyedrops administered after corneal surgery or in cases of corneal disease. The topical ophthalmic application of the vitamin D of this invention is highly effective for ophthalmic patients whose vitamin D intake is insufficient, or who suffer from impaired kidney or liver function. Since the effects of topical application of the vitamin D of this invention to the cornea are dependent on the activity of the keratocytes and differentiated fibroblasts, there will be little change in the invention's effectiveness in regulating wound healing of ocular tissue even if it contains an excessive concentration of the vitamin D ergocalciferol or cholecalciferol. In other words, in contrast to active vitamin D, the effectiveness of the vitamin D cholecalciferol in regulating corneal cell hyperplasia and metabolite production in injured corneas was not reduced even at relatively high concentrations. In contrast to active vitamin D, it is known that the vitamins D ergocalciferol and cholecalciferol are safe and do not cause the well known side-effect hypercalcemia. Moreover, topical administration of the vitamin D of this invention to the anterior segment does not pose the risk of vitamin D excess, which can occur as a result of excess vitamin D intake. The vitamin D of this invention can be administered safely to the anterior segment because vitamin D has no cytotoxicity. The vitamins D ergocalciferol and cholecalciferol should not exhibit vitamin D toxicity even when used with other medicines.

By protecting the eyes against harmful UV radiation, the ophthalmic composition of vitamin D of this invention can prevent corneal diseases such as photokeratitis, corneal ulceration and corneal dystrophy which are caused by UV radiation. Moreover, it is possible to reduce opacity of the lenticular capsule after cataract surgery by using an ophthalmic composition of the vitamin D ergocalciferol or cholecalciferol of this invention.

Topical use of either provitamin D, previtamin D, vitamin D, active vitamin D, vitamin K or an analog of one of these in this invention on the skin can protect the skin from harmful UV light. Moreover, since it can also be applied as an ophthalmic composition, the provitamin D, previtamin D, vitamin D, active vitamin D, vitamin K and analogs of these should cause no side-effects even if they enter the eyes.

What is claimed is:

1. A therapeutic method, comprising the step of preventing or treating keratoconjunctival dryness or keratoconjunctivitis sicca in mammals in need thereof by administering to a mammal a pharmaceutical having an effective ingredient selected from the group of vitamin D, active vitamin D formed by hydroxylation of the carbon C1 position of the A-ring of the sterol nucleus, side-chain carbon C25, or both C1 and C25, and analogs thereof.

2. A therapeutic method comprising the step of preventing or treating keratoconjunctival dryness or keratoconjunctivitis sicca in mammals in need thereof by administering topically to a mammalian eye a pharmaceutical having an effective ingredient selected from the group of vitamin D, active vitamin D formed by hydroxylation of the carbon C1 position of the A-ring of the sterol nucleus, side-chain carbon C25, or both C1 nd C25, and analogs thereof.

3. A therapeutic method, comprising the step of treating keratoconjunctival dryness or keratoconjunctivitis sicca in mammals by administering to a mammal a pharmaceutical having an effective ingredient selected from the group of vitamin D, active vitamin D formed by hydroxylation of the carbon C1 position of the A-ring of the sterol nucleus, side-chain carbon C-25, or both C1 and C25, and analogs thereof.

4. A therapeutic method comprising the step of treating keratoconjunctival dryness or keratoconjunctivitis sicca in mammals by administering topically to a mammalian eye a pharmaceutical having an effective ingredient selected from the group of vitamin D, active vitamin D formed by hydroxylation of the carbon C1 position of the A-ring of the sterol nucleus, side-chain carbon C25, or both C1 and C25, and analogs thereof.

* * * * *

UNITED STATES PATENT AND TRADEMARK OFFICE
CERTIFICATE OF CORRECTION

PATENT NO. : 6,162,801
DATED : December 19, 2000
INVENTOR(S) : Kiyoshi Kita

It is certified that error appears in the above-identified patent and that said Letters Patent is hereby corrected as shown below:

Title page,
Item [56], References Cited,
"FOREIGN PATENT DOCUMENTS,"
add -- 4-43887    6/17/88    JAPAN --

"OTHER PUBLICATIONS" change
"Proc. Soc. Exptl. Biol. Med., 1992;20:80-81, U.S.A.
Proc. Soc. Exptl. Biol. Med., 1992;20:81-85, U.S.A."
to
-- Proc. Soc. Exptl. Biol. Med., 1922;20:80-81, U.S.A.
Proc. Soc. Exptl. Biol. Med., 1922;20:80-81, U.S.A. --

Column 16,
Line 21, after "C1" change "nd" to -- and --

Signed and Sealed this

Twenty-third Day of October, 2001

Attest:

NICHOLAS P. GODICI
Attesting Officer    Acting Director of the United States Patent and Trademark Office